United States Patent
Zviman et al.

(10) Patent No.: US 7,473,395 B2
(45) Date of Patent: Jan. 6, 2009

(54) HYPOTHERMIA INDUCTION DEVICE

(76) Inventors: Menekhem M. Zviman, 1433 Primrose Pl., Belcamp, MD (US) 21017; Henry R. Halperin, 7708 Crossland Rd., Baltimore, MD (US) 21208

(*) Notice: Subject to any disclaimer, the term of this patent is extended or adjusted under 35 U.S.C. 154(b) by 276 days.

(21) Appl. No.: 11/204,998

(22) Filed: Aug. 17, 2005

(65) Prior Publication Data
US 2006/0041217 A1     Feb. 23, 2006

Related U.S. Application Data

(60) Provisional application No. 60/602,159, filed on Aug. 17, 2004, provisional application No. 60/619,819, filed on Oct. 18, 2004.

(51) Int. Cl.
*A61M 37/00* (2006.01)
*C02F 1/44* (2006.01)

(52) U.S. Cl. ............... 422/46; 604/6.11; 604/5.01; 604/6.09; 604/6.1; 604/6.15; 210/739; 210/741

(58) Field of Classification Search ............... 604/4.01, 604/5.01, 6.05, 6.11, 6.13; 422/44–46; 210/739; 210/741
See application file for complete search history.

(56) References Cited

U.S. PATENT DOCUMENTS

| | | | | |
|---|---|---|---|---|
| 4,657,529 A | * | 4/1987 | Prince et al. | 604/6.11 |
| 4,776,837 A | * | 10/1988 | Kopp | 604/6.05 |
| 5,817,045 A | * | 10/1998 | Sever, Jr. | 604/6.11 |
| 5,823,987 A | * | 10/1998 | Elgas et al. | 604/6.13 |
| 6,565,807 B1 | * | 5/2003 | Patterson et al. | 422/45 |
| 6,585,675 B1 | * | 7/2003 | O'Mahony et al. | 604/4.01 |

* cited by examiner

*Primary Examiner*—Leslie R Deak
(74) *Attorney, Agent, or Firm*—Nixon & Vanderhye P.C.

(57) ABSTRACT

A system for rapid induction of indication of hypothermia especially of the heart and brain during cardiac arrest and normal circulation. The device recirculates blood through an extracorporeal circuit using a single venous access. The blood can be cooled and/or treated before reentry to the vascular system. The device maximizes the cooling rate by optimizing the blood withdrawal rate. Cooling of the brain is achieved by flow of cooled blood from the thorax to the head. During cardiac arrest, the blood flow is generated by cardiopulmonary resuscitation.

15 Claims, 3 Drawing Sheets

HYPOTHERMIA INDUCTION DEVICE

This application claims the benefit of the filing dates of U.S. Provisional Application Ser. Nos. 60/602,159 and 60/619,819, filed Aug. 17, 2004 and Oct. 18, 2004, respectively, by Dr. Halperin and Dr. Zviman, both of which are incorporated herein by reference in their entireties.

BACKGROUND OF THE INVENTION

1. Field of Invention

This invention relates generally to the field of methods and apparatus for treating patients with brain and heart ischemia by rapid induction of hypothermia. More specifically, this invention relates to devices for rapid induction of brain and heart hypothermia during cardiac arrest.

2. Background Art

Mild hypothermia is recommended for out-of-hospital arrest patients where the initial rhythm was ventricular fibrillation (VF). Mild hypothermia (32-34° C.) has been shown to improve the outcomes of cardiac arrest, stroke, brain trauma, acute myocardial infarct and more. Recent studies suggest that hypothermia should be induced early and quickly.

A variety of methods demonstrated the ability to cool the brain and heart. Most commonly, external cooling by means of ice bags or chilling blankets is used. Other external devices such as a head cover were described to cool primarily the head.

Invasive, endocorporeal cooling of blood is described in U.S. Pat. No. 6,726,710 B2 and U.S. Pat. No. 6,849,083 B2. These patents describe whole body cooling by cooling the blood via a heat exchanger placed in a catheter inserted to the vena cava.

Cardiopulmonary bypass is used routinely to cool the heart. Several methods, based on bypass configuration, were demonstrated to rapidly cool the brain. More recently, methods of cooling through two veins were described. Furse et al. teach delivering cold saline to the brain via cannulation of vertebral artery after occlusion of the bilateral common carotid and the left vertebral arteries and drainage of excess fluid via microfiltration probe in the cortices. [M. Furuse, T. Ohta, T. Ikenaga, Y. M. Liang, N. Isono, T. Kuroiwa, and M. C. Preul, "Effects of intravascular perfusion of cooled crystalloid solution on cold-induced brain injury using an extracorporeal cooling-filtration system," *Acta Neurochirurgica*, vol. 145, pp. 983-993, 2003.] Behringer et al. teach cooling by circulating blood between to two venous accesses through a heat exchanger. However, none of the prior art describes a system that uses only one venous access to extracorporeally cool blood. [W. Behringer, P. Safar, X. Wu, A. Nozari, A. Abdullah, S. W. Stezoski, and S. A. Tisherman, "Veno-venous extracorporeal blood shunt cooling to induce mild hypothermia in dog experiments and review of cooling methods," *Resuscitation*, vol. 54, pp. 89-98, 2002.].

Several methods and apparati for withdrawal and infusion of blood have been described. Blood withdrawal pump controllers are described in U.S. Pat. Nos. 5,536,237, 4,657,529 and 6,585,675. The authors of U.S. Pat. Nos. 5,536,237 and 4,657,529 adjust the rate of withdrawal by using a relationship between flow and pressure established via a calibration curve. These authors do not provide a solution for vessel collapse during withdrawal except removal of the needle. U.S. Pat. No. 6,585,675 teaches control of flow rate using a control algorithm that temporarily reverses the flow to overcome vessel collapse. However, none of these methods and apparati uses a single access to the vascular system to perform recirculation. Moreover, none of these provide relief of the vacuum causing the vessel collapse by a shunt to a reservoir before reversing the flow or use a second pump to provide blood flow to open the collapse.

U.S. Pat. No. 6,485,450 teaches infusion of chilled blood or medical fluid and collection of blood for recirculation. This method however, relies on passive collection of blood rather than withdrawal, and this collection is done via separate vascular accesses. None of the references describes cooling the brain by using cold blood flowing to the brain due to cardiopulmonary resuscitation.

BRIEF DESCRIPTION OF THE INVENTION

The apparatus and method according to the invention rapidly cools the heart and brain of patients during cardiopulmonary resuscitation or during normal circulation. The device can be used in an out-of-hospital environment since it requires only a single venous access. Further, cooling of the heart and brain does not need to rely on return to normal circulation. Early hypothermia was shown to increase the likelihood of survival and lessen brain damage.

Blood withdrawn from the patient can be treated by dialysis, ultra-filtration, oxygenation and cell removal concomitant to cooling. Drugs can be delivered rapidly to the heart during cardiopulmonary resuscitation.

The device comprises of a connection to an intravenous catheter, a withdrawal circuit, a reservoir, infusion pump, optional treatment modules to perform dialysis, ultra-filtration, oxygenation and cell removal, a heat exchanger, pressure sensors, and a shunt circuit between the blood reservoir and the withdrawal line and a controller.

The controller maximizes the withdrawal rate by continuously searching for the highest withdrawal rate that does not result in vessel collapse. The controller adjusts the speeds of both the withdrawal and infusion pumps based on the pressures sensed in the corresponding lines and operator defined maximal values. When pressure sensed indicates vessel collapse, the controller stops the withdrawal pump and opens the shunt between the reservoir and the withdrawal line. If the negative pressure does not dissipated during a predetermined duration, the shunt is closed and the withdrawal pump reverses for a short duration. (Alternatively, we can use the infusion pump to inject the volume required to open). When the withdrawal of a predetermined volume is complete, the controller stops the withdrawal pump and starts the infusion pump. Blood from the reservoir, is passed through the treatment modules and through the heat exchanger back to the vein. During cardiac arrest, the cold blood in the thorax is move by the flow generated by cardiopulmonary resuscitation to the brain. During normal circulation, the normal blood flow carries the cold blood to the brain. Based on the temperature of the withdrawn blood the controller adjusts the maximal withdrawal rate to maintain a predetermined temperature.

DETAILED DESCRIPTION OF THE INVENTION

A blood recirculating apparatus has been developed that uses a single venous access. This apparatus provides a blood recirculating apparatus that can quickly cool the heart and brain of patients in both cardiac arrest and normal circulation.

The apparatus may be used for continuously treating blood by dialysis, ultra-filtration, oxygenation and/or cell removal concomitant to cooling or without cooling.

A method has been developed to maximize blood withdrawal rate by using a controller that can be based on a microprocessor. The method provides a technique to overcome blood vessel collapse during blood withdrawal. This method comprises of stopping the withdrawal pump and employing a shunt between the blood reservoir and the withdrawal line thus relieving the vacuum in the line. If, after a predetermined time, the vacuum does not dissipate, the shunt is closed and the withdrawal pump is operated in the reverse direction yielding flow of blood via the collapsed vessel. The method overcomes blood vessel collapse during blood withdrawal by stopping the withdrawal pump and briefly running the infusion pump such that blood flows into the collapsed vessel.

The method and apparatus provide a means to withdraw a predetermined volume of blood into an extracorporeal reservoir and then infuse said volume using the same access into the vascular system. Further, the method and apparatus may be used to withdraw a predetermined volume of blood into an extracorporeal reservoir and then infuse said volume while being cooled using the same access into the vascular system.

Figure 1:
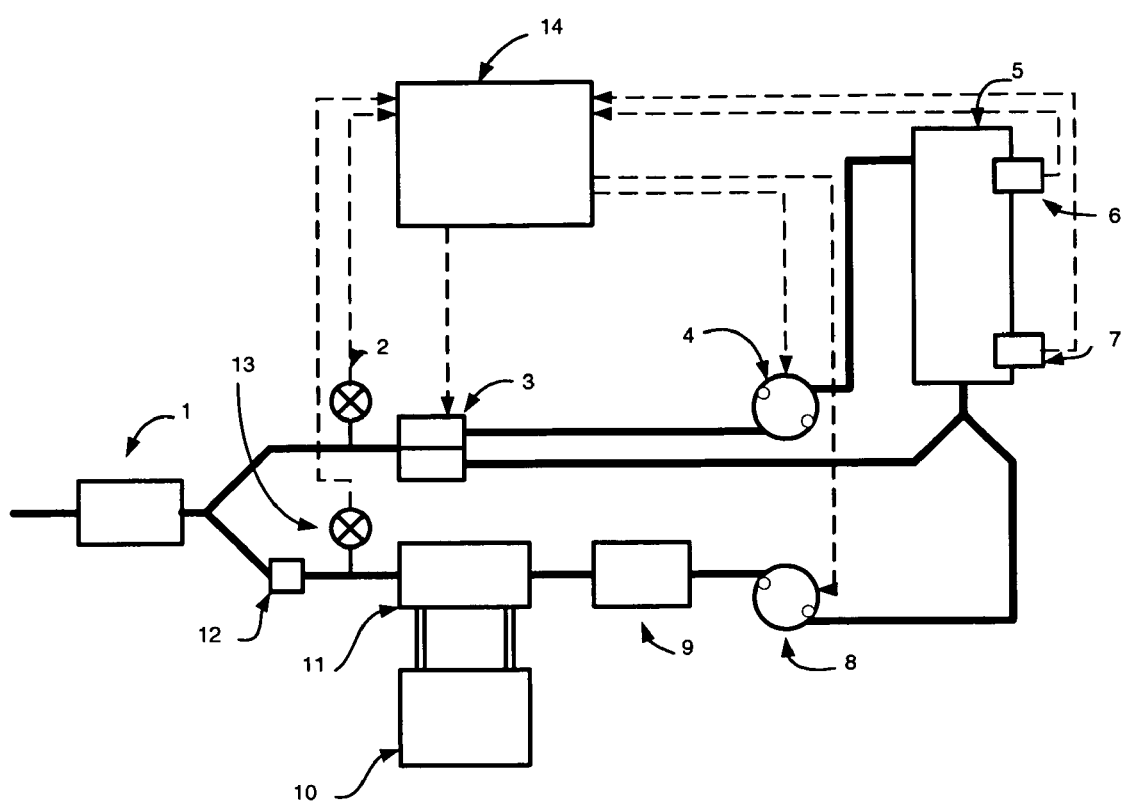
FIG. 1 is a schematic diagram of one embodiment of a rapid hypothermia induction apparatus according to the invention.

FIG. 1 is a schematic diagram of a hypothermia inducing device including a blood circuits. Thick lines in FIG. 1 represent the blood lines in the circuit. Broken lines represent controller inputs and outputs. The arrow at the end of the broken lines represent the sensed data inputted to the controller or control signals generated by the controller.

The extracorporeal blood circuit system is comprised of a connector 1 to the intravenous access catheter, withdrawal pressure sensor 2, a two pole valve 3, a withdrawal pump 4, a blood reservoir 5, a full reservoir detector 6, an empty reservoir detector 7, an infusion pump 8, optional modules to treat blood 9, a chiller 10, a heat exchanger 11, a drug injection port 12, and an infusion pressure sensor 13. The system is regulated by a controller 14, such as a microprocessor having a memory with a stored executable control algorithm(s). The controller receives input signals from the pressure sensors 2 and 13, reservoir detectors 6 and 7, and issues control commands as output signals to regulate the speed and rotational direction of the pumps 4 and 8, and the switch position of the valve 3.

A predetermined volume of medical fluid is infused from the blood reservoir 5 to the blood vessel passing through the optional blood treatment modules 9, and the heat exchanger 11. When the reservoir is empty, a signal from the empty reservoir detector 7 is sent to the controller 14. In response to an empty reservoir, the controller turns the infusion pump 8 off, and pauses for a predetermined duration, e.g., 1 to 5 seconds. After the pause, the controller turns the withdrawal pump 4 on. The valve 3, in a first switch position, connects the withdrawal pump to the venous access connector 1 so that blood flows into the blood reservoir. When the blood level in the reservoir reaches the full reservoir detector 6, the detector sends a signal to the controller. Upon receiving the reservoir full signal, the controller stops the withdrawal pump 4 and restarts the infusion pump 8.

Figure 2:
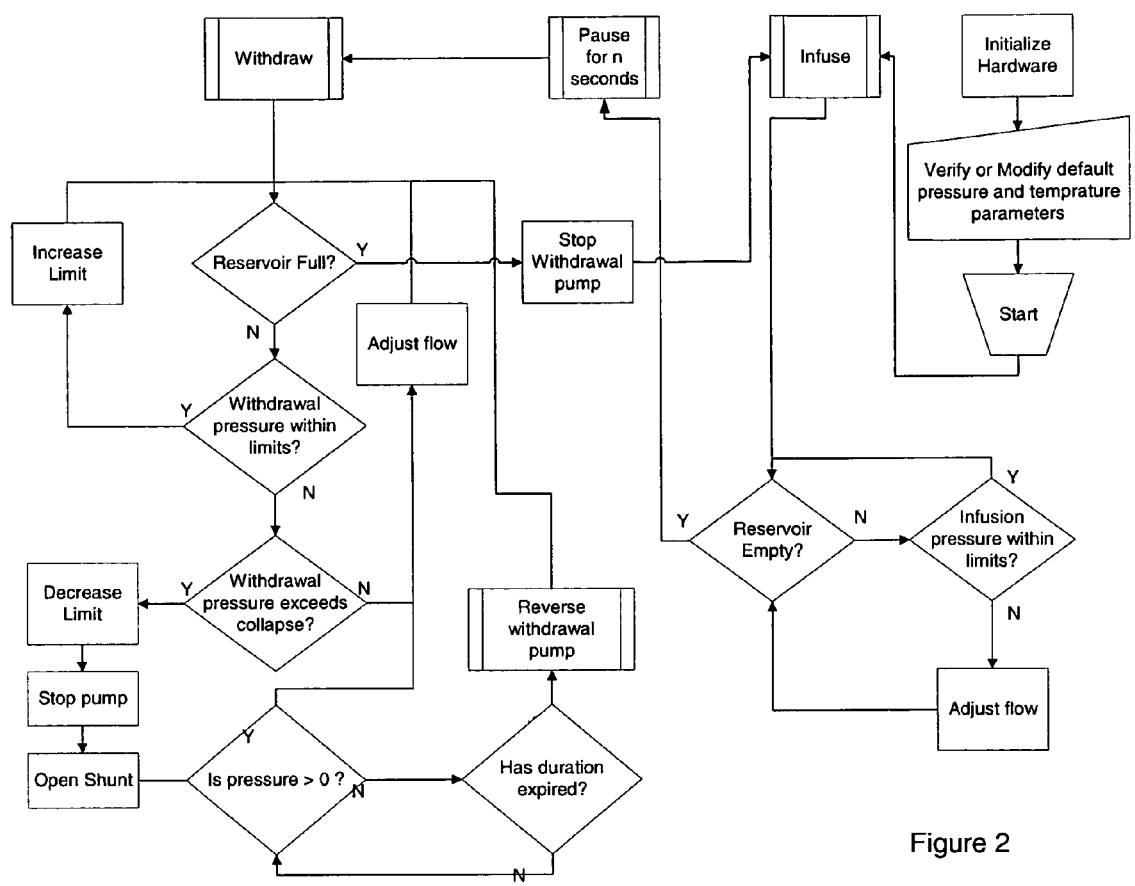
FIG. 2 is a flow chart of the controller algorithm.

FIG. 2 is a flow chart describing an algorithm executed by the controller. After hardware initialization and set parameter verification/modification by the controller, the controller is ready to start the infusion and withdrawal of blood from a patient. When the operator commands the system to start, the controller performs a set of tasks before turning the infusion pump on. When the infusion pump 8 is on, the controller continuously monitors the empty reservoir detector 7. The controller also continuously monitors the infusion pressure 13 and adjusts the speed of the pump 8 to achieve a predetermined infusion pressure.

When the empty reservoir detector signals that the reservoir is empty, the controller 14 stops the infusion pump 8 and enters into a pause for a predetermined duration, e.g., 1 to 5 seconds. After the pause, the controller turns on the withdrawal pump 14 to withdraw blood from the patient and through to the venous connector 1. The valve 3 is set by the controller so that a negative pressure, e.g., below atmospheric, applied by the withdrawal pump 4 draws blood from the patient through the connector 1.

During blood withdrawal, the controller continuously monitors the full reservoir detector 6 and the withdrawal pressure 2. If the withdrawal pressure signal indicates the pressure is out of the limits, e.g., the pressure becomes excessively negative, the controller determines if the withdrawal pressure indicates that a vessel occlusion or collapse has occurred. If vessel occlusion/collapse is detected, the controller stops the withdrawal pump 4 and switches the valve 3 to allow blood from the blood reservoir to flow through to the connector 1 and the occluded/collapsed vein. In this manner, the valve 3 is a shunt to allow blood in the reservoir to dissipate the negative pressure that caused the blood vessel collapse or occlusion.

While the valve operates as a shunt, the controller monitors the withdrawal pressure 2 for a predetermined duration, e.g., 1 to 5 seconds. If the negative pressure dissipates (e.g., sensor 2 detects a rise in the pressure), the controller switches the valve 3 back to its normal state to connect the connector 1 to the withdrawal pump to resume withdrawal of blood from the patient and to the reservoir.

On the other hand, if after the monitoring duration, e.g., 1 to 5 seconds, the negative pressure does not dissipate in response to the valve serving as a shunt, the controller switches the valve 3 back to its normal position and reverses the withdrawal pump to force blood in the blood line back through the valve, connector and into the occluded/collapsed vein for a brief duration, e.g., 1 to 3 seconds. After this brief duration (which is less than the time needed to evacuate the line by the reversed blood pump 4), the controller again reversed the pump to resume normal blood withdrawal. Thereafter, if the pressure sensor 2 again detects an occlusion/collapsed vein with in a short predetermined time period, e.g., 5 to 30 seconds, the controller may stop the withdrawal and infusion pumps and issue an alarm for the operator.

When the level of blood fills the reservoir, the full reservoir detector signals the controller, which in turn, stops the withdrawal pump 4 and restarts the infusion pump. This cycle of withdrawal followed by infusion continues until stopped by the operator.

Figure 3:
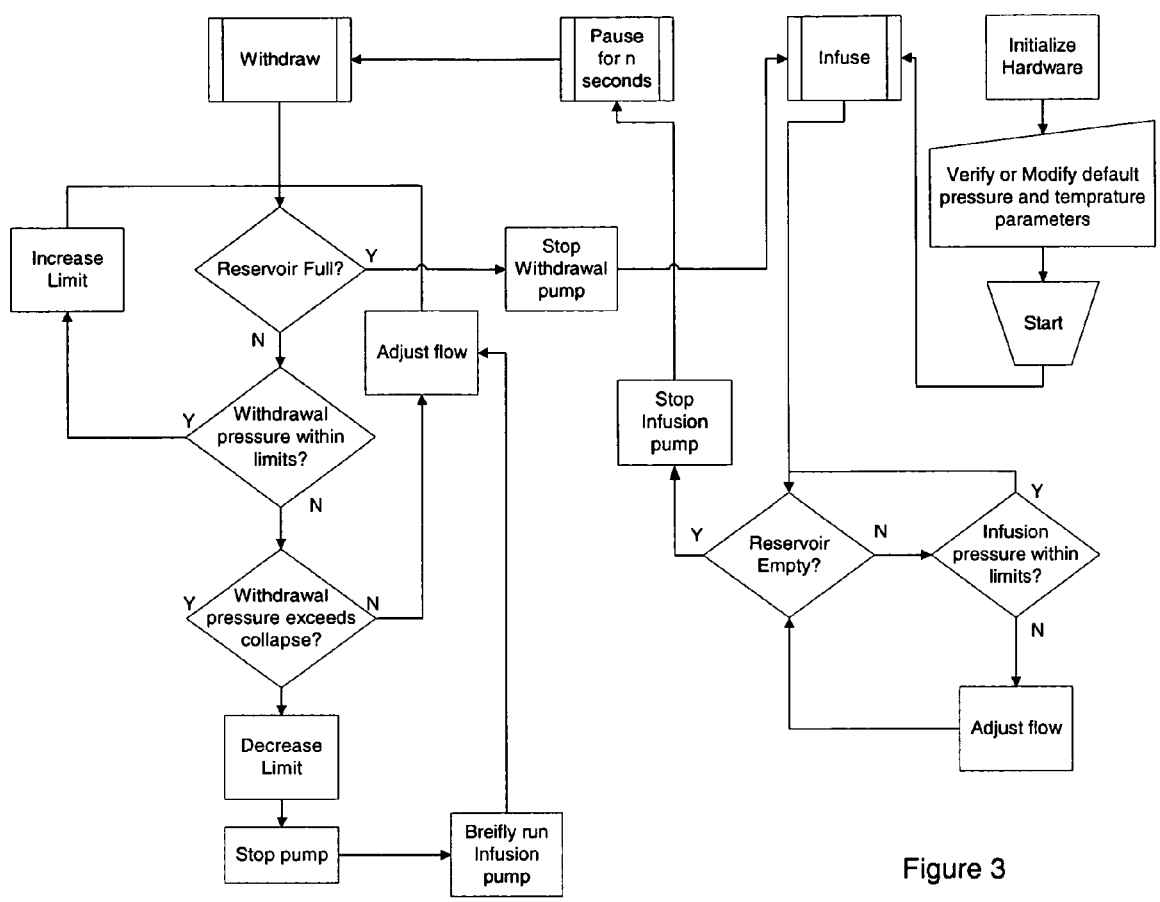
FIG. 3 is a flow chart of a different controller algorithm.

FIG. 3 is a flow chart describing an algorithm used by the controller. Similar to the algorithm described in FIG. 2, the controller monitors the withdrawal pressure for evidence of blood vessel collapse. Upon detection of blood vessel collapse or occlusion, the controller stops the withdrawal pump and briefly runs the infusion pump to relieve the negative withdrawal pressure at the connector 1. After a small volume of blood is infused and negative pressure is dissipated, the controller stops the infusion pump and restarts the withdrawal pump 4 to resume normal withdrawal resumes. An air bubble detector (not shown) may be included in the connector or in the blood lines between the connector and pumps 4, 8 to ensure that an air bubble in the lines is not infused into the patient. The controller may stop the pumps 4, 8 upon detection of an air bubble.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method to recirculate blood through an extracorporeal circuit having a withdrawal pump and an infusion pump the method comprising:
   a. intermittently withdrawing and infusing the blood from and to a blood flow passage in the extracorporeal circuit via a single venous access to a mammalian patient;
   b. applying an algorithm to maximize withdrawal rate;
   c. detecting a withdrawal blood vessel occlusion;
   d. stopping the withdrawal of blood if the occlusion occurs and relieving a vacuum caused by the occlusion by opening an shunt to a blood reservoir to allow blood in the reservoir to flow into the blood flow passage of the circuit:
   e. if the occlusion does not open within a predetermined time period, reversing the withdrawal pump to create flow through the blood flow passage to the occluded vessel;
   f. if the occlusion does not open within a second predetermined time period, infusing a volume of blood using the infusion pump;
   g. resuming withdrawal until the blood reservoir is filled by a predefined volume of blood;
   h. stopping the withdrawal;
   i. starting infusion of the blood from the reservoir through blood treatment modules and a heat exchanger into the blood vessel;
   j. applying an algorithm to maintain a predefined infusion pressure;
   k. when controller detects that the reservoir is empty, infusion stops and step (b) is resumed.

2. A method for continuously searching for maximal withdrawal rate as in claim 1 wherein the controller increases the maximal withdrawal rate until blood vessel occlusion occurs.

3. A method for continuously searching for maximal withdrawal rate as in claim 1 wherein the controller increases the maximal withdrawal rate to a rate that does not cause blood vessel occlusion.

4. A method for continuously maintaining withdrawal pressure as in claim 1 wherein the controller adjusts the withdrawal rate to achieve a predefined withdrawal pressure.

5. A method for continuously for maintaining infusion pressure as in claim 1 wherein the controller adjusts the infusion rate to achieve a predefined infusion pressure.

6. A method as in claim 1 wherein circuit includes a chiller and the method includes cooling at least one of a heart and brain during cardiopulmonary resuscitation.

7. A method to cool the heart as in claim 6 wherein a volume of cooled blood sufficient to fill all chambers of the heart and the pulmonary vessels is infused.

8. A method to cool the brain during cardiopulmonary resuscitation as in claim 6 wherein cooled blood flow from the thorax due to the cardiopulmonary resuscitation.

9. A method as in claim 1 wherein circuit includes a drug delivery device, and the method includes delivering a drug to the circuit to rapidly deliver drugs to the heart during cardiopulmonary resuscitation.

10. A method as in claim 1 to continuously treat blood using a single venous access.

11. A method as in claim 6 wherein the chiller is electrical.

12. A method as in claim 6 wherein the chiller is not electrical.

13. A method as in claim 6 wherein the cooling effect of cold blood infusion is optimized by delaying the initiation of withdrawal.

14. A method as in claim 1 wherein blood flow rather than pressure is monitored.

15. A method to circulate blood through an extracorporeal circuit having a withdrawal pump, an infusion pump and a blood reservoir, the method comprising:
   intermittently withdrawing and infusing the blood from and to a blood flow passage in the extracorporeal circuit via a single venous access to a mammalian patient;
   upon detection of an occlusion in the venous access during withdrawal of blood into the blood flow passage, temporarily stopping the withdrawal pump and opening an shunt through which blood in a blood reservoir flows into the blood flow passage to apply blood pressure to the venous access;
   after the occlusion has been relieved, resuming the withdrawal pump and the withdrawal of blood while the shunt remains open to direct blood from the blood flow passage into the blood reservoir;
   detecting that a predetermined volume of blood has flowed into the blood reservoir and thereafter closing the shut to prevent further flow of blood into the blood reservoir until the shut is next opened, and
   resuming the intermittent withdrawal and infusion of the blood from and to the blood flow passage.

* * * * *